(12) United States Patent
Myklebust et al.

(10) Patent No.: US 8,192,367 B2
(45) Date of Patent: Jun. 5, 2012

(54) METHOD AND APPARATUS FOR MONITORING RESPIRATION

(75) Inventors: Helge Myklebust, Stavanger (NO); Joar Eilevstjonn, Sandnes (NO); Jon Nysaether, Hafrsfjord (NO)

(73) Assignee: Laerdal Medical AS, Stavanger (NO)

( * ) Notice: Subject to any disclaimer, the term of this patent is extended or adjusted under 35 U.S.C. 154(b) by 616 days.

(21) Appl. No.: 12/024,937

(22) Filed: Feb. 1, 2008

(65) Prior Publication Data

US 2008/0214948 A1     Sep. 4, 2008

Related U.S. Application Data

(60) Provisional application No. 60/887,819, filed on Feb. 2, 2007.

(30) Foreign Application Priority Data

Feb. 2, 2007  (GB) .................................. 0702078.7

(51) Int. Cl.
*A61B 5/08* (2006.01)
(52) U.S. Cl. ........................................................ 600/538
(58) Field of Classification Search .......... 600/529–543; 482/13
See application file for complete search history.

(56) References Cited

U.S. PATENT DOCUMENTS

| | | | | |
|---|---|---|---|---|
| 4,259,967 A * | 4/1981 | Vooren et al. ................. | 600/533 |
| 5,330,514 A * | 7/1994 | Egelandsdal et al. ......... | 434/265 |
| 5,347,843 A * | 9/1994 | Orr et al. ........................ | 73/1.34 |
| 5,379,650 A * | 1/1995 | Kofoed et al. ................. | 73/861.52 |
| 5,727,594 A * | 3/1998 | Choksi ............................ | 137/859 |
| 6,203,502 B1 | 3/2001 | Hilgendorf et al. ............ | 600/538 |
| 6,224,560 B1 * | 5/2001 | Gazula et al. .................. | 600/538 |
| 6,544,192 B2 * | 4/2003 | Starr et al. ..................... | 600/538 |
| 7,004,168 B2 * | 2/2006 | Mace et al. ................. | 128/206.21 |
| 2004/0249300 A1 * | 12/2004 | Miller ........................... | 600/532 |

FOREIGN PATENT DOCUMENTS

WO      95/06234      3/1995

OTHER PUBLICATIONS

Abella, Benjamin S., et al., "Quality of Cardiopulmonary Resuscitation During In-Hospital Cardiac Arrest", JAMA, vol. 293, No. 3, Jan. 19, 2005, pp. 305-310.
Aufderheide, Tom P., et al., "Death by Hyperventilation: A Common and Life-Threatening Problem During Cardiopulmonary Resuscitation", Crit Care Med, vol. 32, No. 9 (Suppl.), Sep. 2004, pp. S345-S351.

* cited by examiner

*Primary Examiner* — Patricia Mallari
*Assistant Examiner* — Christian Jang
(74) *Attorney, Agent, or Firm* — Dorsey & Whitney LLP

(57) ABSTRACT

A device for monitoring respiration comprises a duct, a flow restricting element in the duct, and a pressure sensor arranged in the duct. The pressure sensor measures a pressure drop across the flow restricting element as a pressure difference between a pressure at a location in the duct on a first side of the flow restricting element and a substantially constant pressure on a second side of the flow restricting element opposite the first side.

17 Claims, 3 Drawing Sheets

METHOD AND APPARATUS FOR MONITORING RESPIRATION

CROSS-REFERENCE TO RELATED APPLICATIONS

This application claims the benefit of U.S. Provisional Application No. 60/887,819, filed Feb. 2, 2007, and GB Application No. 0702078.7, filed Feb. 2, 2007. The entire disclosure of the prior applications are considered to be part of the disclosure of the instant application and are hereby incorporated by reference therein.

TECHNICAL FIELD

Embodiments of the invention relate to physiological monitors, and, more particularly, to respiration monitoring apparatus and methods thereof.

BACKGROUND OF THE INVENTION

In many situations there is a need for monitoring a patient's respiration or to provide ventilations to a patient that is not breathing. Such situations might include cardiac arrest, respiratory obstruction, asthma, chronic obstructive pulmonary disease (COPD), heart failure, major trauma, overdose, seizure, sepsis and during anesthesia. In the following description the term "respiration" includes both spontaneous and assisted breathing/respiration as well as ventilations.

In some cases, patients with respiratory problems may be unstable and risk losing their respiratory function. Such patients need to be monitored in some way, either manually, for instance, by observing chest rise, or with the help of a respiration monitor system. However, such systems—commonly using a differential pressure flow sensor, or end tidal $CO_2$ sensor—are often too expensive or not readily available in simple mask-and-oxygen scenarios commonly used out-of-hospital.

A common problem in situations where a rescuer will provide ventilations to a patient, e.g. during cardiac arrest, is poor adherence to guidelines for cardiopulmonary resuscitation (CPR). Often, the patient is hyperventilated which is deleterious to the patient. T. P. Aufderheide and K. G. Lurie, "Death by hyperventilation: a common and life-threatening problem during cardiopulmonary resuscitation," *Crit. Care Med*, vol. 32, no. 9 Suppl, pp. S345-51, September 2004 and B. S. Abella, J. P. Alvarado, H. Myklebust, D. P. Edelson, A. Barry, N. O'Hearn, T. L. Vanden Hoek, and L. B. Becker, "Quality of cardiopulmonary resuscitation during in-hospital cardiac arrest," *Jama*, vol. 293, no. 3, pp. 305-10, Jan. 19, 2005 describe this problem. A solution to this problem is to have a device that detects ventilations and provides feedback on ventilation performance. Ventilations can, for instance, be detected by measuring the impedance change between defibrillator pads. However, impedance signals are often highly susceptible to noise (e.g. compression artifacts) and baseline drift problems requiring advanced and often expensive solutions. Also, the ventilation volume can not be measured using an impedance signal due to the variations of human physiology.

By help of flow sensors in the ventilation path, ventilation activity can be monitored and the ventilation volume assessed by integrating the flow. Flow sensors are typically based on the Venturi principle, i.e., the pressure drop associated with a flow restriction is measured. However, in order to achieve a high level of accuracy, this method requires a restriction with a very sophisticated geometry. This may often be forbiddingly expensive for a single-use unit. Single-use is normally desired or required for respiration measurements due to the risk of cross-contamination between patients.

The Venturi principle also has the disadvantage that two pressure outlets are needed from the restriction, which may complicate the geometry and increase cost. In addition, two pressure sensors are needed to measure the pressure drop in the restriction, which may increase cost. Alternatively, the two pressure sensors may be replaced with a single differential pressure sensor. If a differential pressure sensor is used, the output from the sensor can, however, only be used to assess flow, and not to monitor the absolute airway pressure, which may be important for detecting mask leakage, airway occlusion etc. Additionally, Venturi measurements are also known to be unstable in conditions of turbulent flow.

VentCheck™ by Respironics is a hand-held respiratory mechanics monitor that measures flow and pressure at the patient's airway. This monitor is designed for use on adults, pediatrics, and neonatal patients and can be used on any conventional ventilator. This monitor uses differential pressure single-use flow sensors to provide a breath-by-breath picture of the patient's respiratory status.

U.S. Pat. No. 6,203,502 describes a respiratory function monitoring device comprising a flow sensor and a conversion device. The device comprises two pressure transducers, one for measuring differential pressure corresponding to a gas flow rate, and a second to measure static airway pressure.

International Application WO 95/06234 describes a differential pressure sensor for measuring respiratory gas flow. The sensor is designed to have the capability of accommodating a wide variety of gas flow inlet conditions while employing a minimum of added system volume or resistance to flow.

U.S. Pat. No. 6,544,192 describes a patient monitoring apparatus for quantatively measuring a physiological characteristic of a patient. A first patient interface communicates with an airway of a patient such that substantially all gas inhaled and exhaled by the patient passes through the patient interface. One or more vent elements associated with the first patient interface communicate the first patient interface with an ambient atmosphere so that a pressure differential is created between the pressure in the first patient interface and the pressure of the ambient atmosphere. A sensor communicates with the first patient interface and measures a fluid characteristic resulting from this pressure differential and outputs a first signal indicative of that characteristic.

There is, therefore, a need for a simple and inexpensive device and method for monitoring respiration/ventilation of a person to overcome the above mentioned problems associated with the prior art.

DETAILED DESCRIPTION OF PREFERRED EMBODIMENTS

Certain details are set forth below to provide a sufficient understanding of embodiments of the invention. However, it will be clear to one skilled in the art that embodiments of the invention may be practiced without these particular details. Moreover, the particular embodiments of the present invention described herein are provided by way of example and should not be used to limit the scope of the invention to these particular embodiments.

Figure 1A:
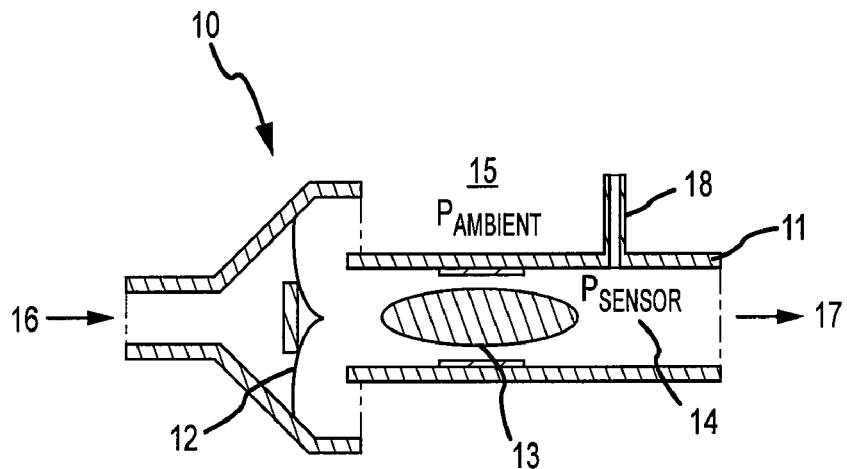
FIGS. 1*a*-1*c* illustrate an embodiment of the invention for use in ventilation monitoring.

FIG. 1a illustrates a monitoring device 10 in accordance with an embodiment of the invention. The monitoring device 10 may include a duct 11 and a restriction 13 arranged inside the duct 11, restricting the fluid (e.g., gas, air, or other fluidal substance) flow in the duct. A resuscitator bag/bellow 16 and a patient interface 17, such as a face/respiratory mask, are connected to the monitoring device 10 on opposite ends of the duct 11. The monitoring device 10 may further include a pressure sensor 14 arranged in the duct at the patient side of the restriction 13 and having a pressure outlet 18. The reference number 14 represents the location of the measured pressure, while the physical sensor may be placed in another location and connected to the location of pressure measurement by means of a flexible tube, for example.

The pressure sensor 14 measures a pressure drop across the restriction 13. In one embodiment, the pressure drop across the restriction 13 is measured as the pressure difference between the pressure sensor 14 arranged at one side of the restriction 13 (e.g., between the patient and the restriction 13) and a known, substantially constant pressure arranged at the other side of the restriction 13. In this way, the flow (both volume flow and mass flow) may be calculated directly from a single pressure measurement. The point of known pressure is preferably ambient pressure in one embodiment. It may alternatively be another point where the pressure can be assumed to be a constant pressure, for instance, associated with an overpressure valve in another embodiment.

The pressure sensor 14 may be an absolute pressure sensor, or it may be a differential pressure sensor coupled between the point of pressure measurement and the known reference pressure (e.g., ambient). To avoid pressure fluctuations that may compromise accuracy, care should be taken to assure a low or constant flow rate, or at least laminar flow, at the point of pressure measurement.

In one embodiment, the restriction 13 is shaped to ensure that the flow velocity is substantially equal on both sides of the restriction 13. This will, for example, be achieved by a symmetric shaped restriction. In another embodiment, the restriction 13 is preferably shaped in such a way that the flow through it is laminar, although the operating principle of the monitoring device 10 still applies with a turbulent flow.

The duct 11 may be any duct arranged in connection with the airway of a person. In one embodiment, the duct 11 is connected to a respiration device, for example, a respiratory mask, a tracheal tube, a bellow, anesthesia mask, etc. In an alternative embodiment, the duct 11 is integrated in a respiration device that may be a respiratory mask, a tracheal tube, a bellow, anesthesia mask etc. When the duct 11 is integrated in a respiration device, the restriction 13 may be constituted by a restriction already in the respiration device, such as a valve, choke, etc.

Figure 1B:
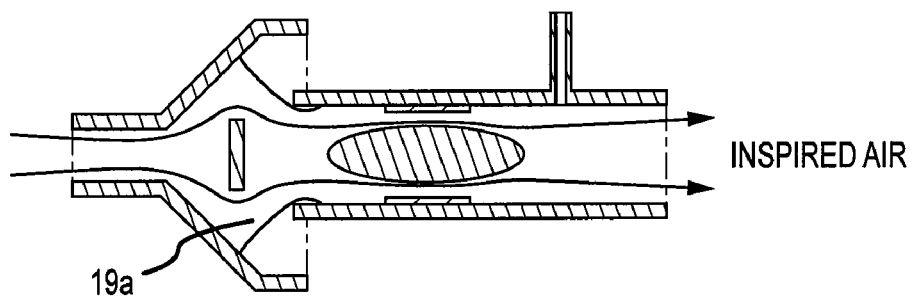
Figure 1C:
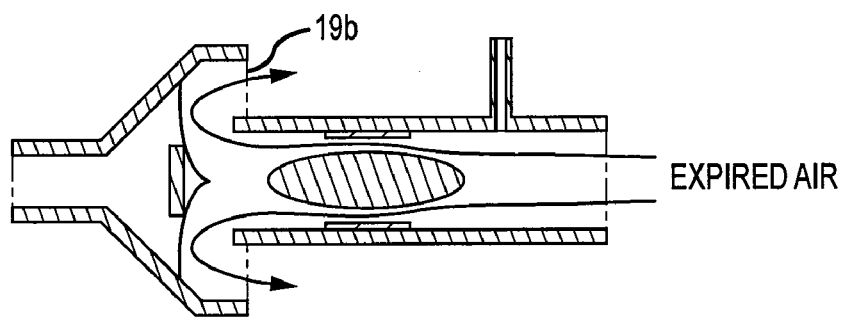

In one embodiment, the monitoring device 10 may include a one-way valve with known flow resistance connected to the duct 11. The one-way valve may be a one-way valve of a respiration device connected to the duct 11, or a separate valve. The one-way valve may have an opening to ambient, the surroundings, where the opening may constitute the point of the known, substantially constant pressure of the device. In the case of a separate one-way valve, the monitoring device 10 may be connected to any other device without the need for knowing the flow resistance of the other device. As shown in FIGS. 1a-1c, a one-way valve 12 comprising inlet valve 19a and outlet valve 19b is arranged at the end of the duct 11 facing away from the patient.

The monitoring device 10 may be used to measure expiration volume from a patient who is ventilated by use of a resuscitator bag with a face mask (both not shown, but their locations are indicated in the figure by respective reference numbers 16 and 17). A resuscitator bag typically comprises inlet and outlet one-way valve(s) to separate the inspiration and expiration flow paths. The purpose of these valves is to allow air from the bag to enter the patient, but not allow air from the patient back into the bag, i.e., the expired air is exhausted to the ambient/surroundings through the outlet valve. In the embodiment of FIGS. 1a-1c, a one-way valve 12 is arranged as a part of the monitoring device 10, but there may be embodiments where the one-way valve 12 is separate from the monitoring device 10, for example, in a resuscitator bag, and is connected to the monitoring device 10 when in use.

FIG. 1b illustrates the situation where air is flowing from the resuscitator bag 16 through the inlet valve 19a and restriction 13 to the patient as inspired air.

FIG. 1c illustrates the opposite situation of FIG. 1b where air is expired by the patient and flows back through the restriction 13 and out to the ambient through the outlet valve 19b.

In one embodiment, the restriction 13 is placed between the pressure sensor outlet 18 and the outlet valve 19b. Thus, during expiration, air flows from the patient, past the pressure sensor 14 and out of the outlet valve 19b through the restriction 13. The pressure drop from the pressure sensor 14 to ambient is thus determined by the flow resistance through the restriction 13 and the outlet valve 19b in series. If the total resistance of this series flow restriction (i.e., the resistance between the pressure sensor and ambient) is known, the overpressure (over ambient) measured by the pressure sensor 14 can be used to determine the flow through the restriction 13. In order to ensure that the total restriction resistance is known, an outlet valve with known characteristics (such as flow resistance) may be connected to the duct 11. By integrating the measured flow during expiration, the expired volume can be calculated. This is a very relevant measure since the important thing is how much air is actually going into the lungs.

If the outlet valve 19b has a suitable flow resistance, the valve can function as the measurement restriction itself and no further restrictions are needed. It should be emphasized that there are many different embodiments of the invention, each of which may be applicable, depending on the application. For example, the restriction 13 can take many different forms. It may, for instance, be associated with an outlet valve or an airway filter of some kind. Also, the restriction 13 and pressure outlet 18 can be made an integral part of a resuscitator bag.

In one embodiment, a flow restriction like the restriction 13 and a pressure sensor outlet like the pressure outlet 18 may be integrated in an airway adapter (not shown) with standardized fittings on both sides. The airway adapter may be for single use or for multiple use. In operation, the airway adapter may be connected between a resuscitator bag on one side and a patient interface (e.g., mask or endotracheal tube) on the other side. Since the measuring principle is dependent on the flow resistance of the outlet valve, this adapter may also comprise a separate outlet valve with a known flow resistance, which blocks the flow to alternative outlet valves with unknown resistance.

In addition to providing a measurement of flow, and thus the volume, the reading from the pressure sensor 14 can be used to detect other important events and situations associated with ventilation or respiration. For instance, if the measured pressure attains elevated values during inspiration, while the measured expiration volume is low, this may be an indication that the airway is occluded. Ventilation parameters such as ventilation rate, inspiration time, and expiration time can also be derived from the pressure reading.

By observing the maximum airway pressure and the corresponding expired volume, the compliance of the lung can be estimated. By observing the flow at the beginning of the expiration phase, the airway resistance may also be calculated. Based on these two parameters, it may be possible to estimate the inspiration flow from the measured pressure. This estimated flow can, for instance, be used to generate a volume or flow waveform of the entire ventilation, and not only of the expiration phase. Also, if the measured expired volume is significantly lower than the calculated inspired volume, mask leakage may be indicated.

Those skilled in the art will realize that the principle described above is fundamentally different from the Venturi principle, although both principles make use of a restriction. In a Venturi flow sensor, the purpose of the restriction is to accelerate the air flow and detect the reduction in pressure that follows from increased fluid speed through Bernoulli's theorem. In contrast, in certain embodiments of the invention, the purpose of the restriction is much the same as that of a resistor in an electrical circuit. Analogous with the voltage drop across a resistor, which is linearly proportional to the electrical current, the pressure drop across a restriction, according to an embodiment of the invention, will be linearly proportional to the flow through the restriction (provided the fluid speed is similar at both ends of the restriction). This linear relationship between pressure drop and flow is an advantage of the embodiments of the invention over the Venturi principle, where there is a quadratic relationship.

Figure 2:
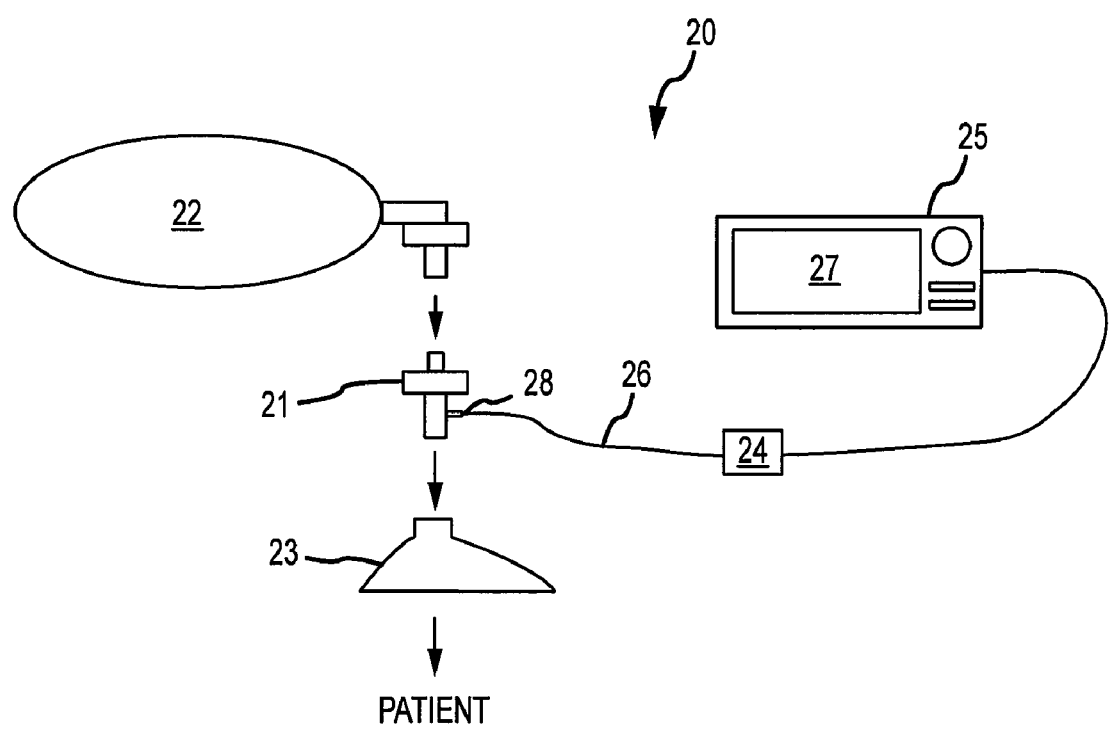
FIG. 2 illustrates an overview of a ventilation monitoring system in accordance with an embodiment of the invention.

FIG. 2 illustrates a ventilation monitoring system 20 according to one embodiment of the invention. The ventilation monitoring system 20 may include a processing unit 25 connected to a pressure sensor 24 for processing the measured pressure signal. The ventilation monitoring system 20 may also include a user interface 27 for providing information regarding the respiration to a user (not shown). The processing unit 25 comprises required electronics (e.g., processor) and the user interface 27 may, for example, comprise display, light emitting diodes, loudspeaker, etc. A restriction, a pressure outlet, and a one-way valve, as those described with respect to FIGS. 1a-1c, are integrated as a part of an airway adapter 21 which may or may not be made for single-use. The airway adapter 21 is connected to a face mask 23 and a resuscitator bag 22. Additional airway filters (not shown), e.g., moisture filters, may be placed between the airway adapter 21 and patient interface, such as the face mask 23. A pressure sensor 24 connected to the processing unit 25 is arranged to be connected to the pressure outlet 28 through tube 26, and measures the pressure at the patient side of the restriction as described with regard to FIG. 1a.

The processing unit 25 may be part of a patient monitor and/or defibrillator system (e.g., AED, compression machine, CPR assist/guidance device, machine ventilator), or it may be a stand-alone unit. The processing unit 25 provides means for acquiring a pressure signal from the pressure sensor 24 (which could reside in the processing unit, airway adapter or stand-alone unit) and a processor to process this pressure signal. An algorithm which may be used to detect and perform ventilation measurements is outlined below. The processing unit 25 might also have means to provide feedback and/or guidance on ventilation performance to the rescuer and to store data for later use. Such feedback may include numeric values, text, graphs or graphics on a display (visual feedback) or sound or voice prompts through a loudspeaker (audible feedback). In one embodiment, the processing unit 25 can calculate flow values from the measured pressure drop. In another embodiment, the processing unit 25 can calculate flow values from the linear relationship between pressure drop and flow. The processing unit 25 may also be able to calculate respired volume from the flow values or from the measured pressure drop.

Despite the depiction in FIG. 2, the pressure sensor 24 and processing unit 25 might be connected to each other by means of a tube (from pressure outlet to pressure sensor), electrical wires (if pressure sensor is part of the airway adapter), or wireless transmission using, for example, Bluetooth, Wi-Fi, or other wireless communication technology. The pressure sensor 24 provides a pressure signal by means of which ventilations can be detected and ventilation parameters calculated.

Figure 3:
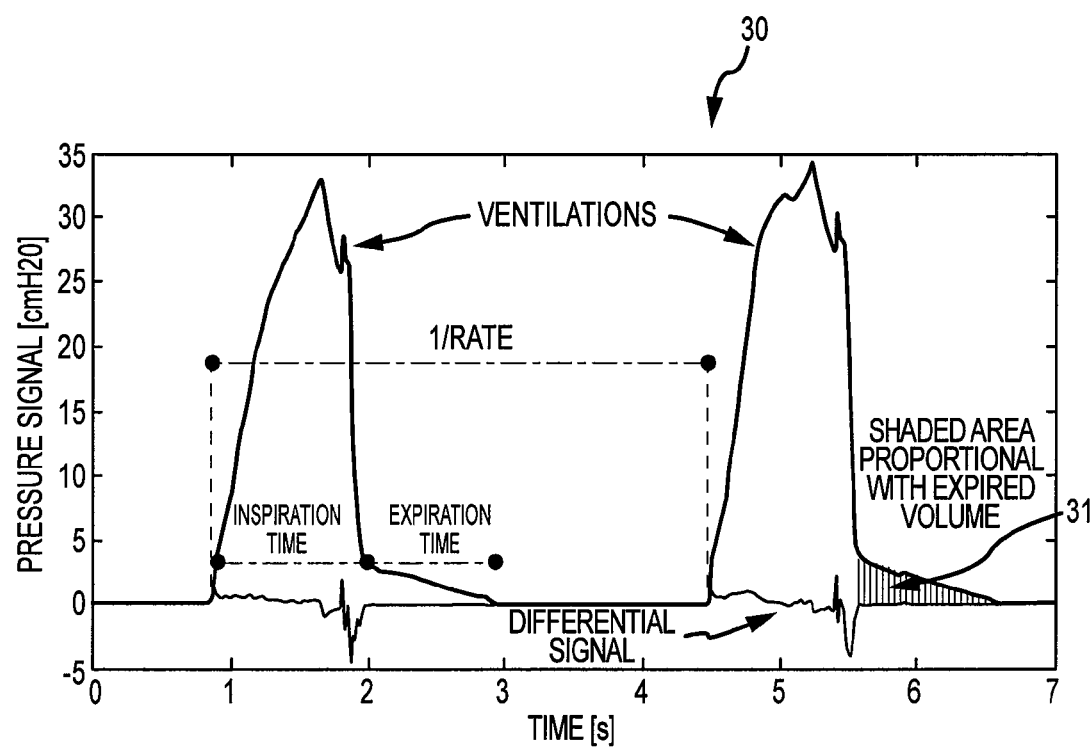
FIG. 3 illustrates an example of a pressure signal achieved by means in accordance with an embodiment of the invention.

FIG. 3 illustrates a timing diagram 30 of an example of a pressure signal, p_sensor, provided by a pressure sensor such as described in FIGS. 1a-1c and FIG. 2. The pressure is measured relative to ambient pressure. The features of ventilations can be detected and processed from the pressure signal as outlined below.

1. A ventilation can be easily detected, e.g., through simple time-domain thresholding of the pressure signal.

2. The ventilation rate will be the inverse of the time between two ventilations.

3. The expired volume of a ventilation is proportional to the area 31 shaded in FIG. 3, i.e., the area under the ventilation pressure signal after the initial rapid decrease in pressure until pressure reaches a zero level. This area may be found by integration, i.e., summing up digitized signal samples of the amplitude to achieve the integration from an integration start time to an integration stop time. To find the integration start time, the differential signal can be used (i.e. first derivative of the pressure signal). When the differential signal goes below a negative threshold, the integration start time can be set when the differential signal returns to a near zero threshold. Alternatively, the integration start time could be when the pressure goes below a certain percentage of peak ventilation pressure. Integration can be stopped when the pressure signal reaches a near zero/baseline value. A timeout can be used if the pressure signal for some reason never reaches this near zero/baseline value, either to stop or cancel integration. The area calculated through integration is approximately linearly proportional with the volume of the expired air. The proportionality coefficient can be found through calibration of the system, or if the resistance R from the pressure sensor to ambient is known, the expired volume can be found by integrating the flow $F(t)=dV\_exp/dt=.p\_sensor(t)/R$.

4. The inspiration time (inflation/insufflation time) can be found by taking the time from start of ventilation (e.g., the detection threshold) to the integration start time.

5. The expiration time can be found by taking the time from integration start to integration stop.

6. The compliance of the lung, C_lung, can be measured as the ratio of the expired volume to the maximum pressure. This can be measured for the previous ventilation or as an average across several ventilations.

7. Airway resistance, R_airway, can be measured by observing the following relationship between lung pressure p_lung(t) and measured pressure p_sensor(t) during expiration: R is the flow resistance from the pressure sensor to ambient through the restriction.

$$p\_\text{lung}(t)=R\_\text{airway}*F(t)+p\_\text{sensor}(t)=(R\_\text{airway}/R+1)p\_\text{sensor}(t)$$

From this equation, R_airway can, for instance, be estimated at the onset of expiration, at $t=t_e$.

We can then write:

$$R\_airway = R*(p\_lung(t_e)p\_sensor(t_e) - 1)$$

To find a value for $p\_lung(t_e)$, we can assume that the pressure in the lung is equal to either the maximum pressure of the ventilation $p\_max$, or to the measured pressure just before expiration starts and pressure rapidly drops. $p\_sensor(t_e)$ is found as the measured pressure just after expiration has started.

6. The inspired volume can be estimated based on the maximum pressure of this ventilation and the lung compliance measured for previous ventilations: $V\_insp = p\_max * C\_lung$.

7. Flow $F(t)$ and volume $V\_lung(t)$ curves can be calculated (and displayed) as a function of time, both during inspiration and expiration. During inspiration: $p\_sensor(t) = R\_airway*F(t) + V\_lung(t)/C\_lung$.

Noting that flow is the derivative of lung volume, $F(t) = dV\_lung/dt$, this is identified as a differential equation that can be solved numerically to give real time flow and volume curves. Values for airway resistance and lung compliance can be found by analyzing previous ventilations as discussed above. During expiration: $F(t) = p\_sensor(t)/R$. As explained above, volume is found by integration.

8. Intrathoracic (lung) pressure, $p\_lung(t)$, can be calculated as a function of time. This can be especially relevant during chest compressions, since blood flow during CPR is believed to be generated partly by fluctuations in intrathoracic pressure. By monitoring the intrathoracic pressure during compressions, it is thus possible to get an indication of how efficient the compressions are in generating blood flow. For instance, compressions can be judged to be efficient when the maximum pressure in the lungs exceeds a certain threshold for each compression, for instance 30 cmH$_2$O. The pressure, or an interpretation of compression efficacy based thereon, can be fed back to the rescuer as an indication of whether or not he/she should compress more forcefully. If ventilations are not carried out simultaneously, or during expiration, the lung pressure during compression is given by $p\_lung(t) = p\_sensor(t) * (R\_airway/R + 1)$.

In another example, an embodiment of the invention may be adapted to measure spontaneous respiration. According to this embodiment, the same sensor and processing unit could be used for the ventilation monitor described with respect to FIGS. 1a-1c and FIG. 2. However, the algorithm might be altered since the pressures associated with respiration are somewhat different from ventilation. A patient's own respirations will have smaller peak pressures than a ventilation and will also be bipolar—i.e., during the inspiration phase the pressure will be negative and during the expiration phase the pressure will be positive. The respiration detection algorithm can then utilize and combine both a negative and positive pressure threshold.

Alternatively, the pressure sensor may be integrated in a simple mask, e.g. as used in supplying oxygen to a patient with respiratory problems, but not respiratory arrest. In this application, pressure may be measured inside the mask. If the flow resistance from the mask to ambient is known, this could work as the restriction and thus enable expiration volume calculation. However, in any case, the pressure signal provided will be sufficient to monitor other parameters such as respiration rate, and most importantly, to monitor whether the patient breathes or not.

Embodiments of the invention may also be combined with additional sensors to provide better assessment of the status of the patient and to provide feedback of rescue efforts. Such additional sensors may include SPO2, ETCO2, ECG, impedance, and a compression sensor.

Another application of embodiments of the invention is in CPR training manikins and simulators. As for patient use, a flow restriction with known characteristics is placed in the expiration path between a pressure sensor and ambient pressure. The sensor is then used to measure parameters (including volume) on the ventilations given to the manikin. In this way valuable feedback can be given to the trainee in order to enhance his/her performance.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A system for monitoring respiration, comprising:
   a duct configured to allow a fluid to flow therethrough;
   a flow restricting element in the duct, the flow restricting element having a flow resistance, the flow restricting element shaped symmetrically with respect to an axis perpendicular to a direction of flow such that, in operation, velocity of the fluid is substantially equal upstream and downstream of the flow restricting element;
   a single pressure sensor arranged in the duct proximate a patient end of the flow restricting element, the single pressure sensor configured to measure a pressure of the fluid at a single location;
   an outlet valve coupled to an end of the duct opposite the patient end, the outlet valve having a flow resistance, the outlet valve configured to allow the fluid to exit the duct to a substantially constant pressure; and
   a processing unit coupled to the single pressure sensor, the processing unit being configured to determine a flow rate based on the pressure measurement of the fluid from the single pressure sensor relative to the substantially constant pressure and based on the flow resistance of the flow restricting element and the flow resistance of the outlet valve.

2. The system of claim 1 wherein the duct is connected to a respiration device.

3. The system of claim 2 wherein the respiration device comprises one of a respiratory mask, a tracheal tube, and a bellow.

4. The system of claim 1 wherein the duct is integrated in a respiration device.

5. The system of claim 4 wherein the respiration device comprises one of a respiratory mask, a tracheal tube, and a bellow.

6. The system of claim 1 wherein the pressure sensor comprises an absolute pressure sensor.

7. The system of claim 1 wherein the substantially constant pressure is ambient pressure.

8. The system of claim 1 wherein the outlet valve comprises a one-way valve.

9. The system of claim 1, further comprising a user interface for providing information regarding the respiration to a user.

10. The system of claim 1 wherein the processing unit is operable to calculate flow values from a linear relationship between pressure drop and flow.

11. The system of claim 1 wherein the processing unit is operable to calculate respired volume by integrating the flow rate over time.

12. The system of claim 1 wherein the processing unit is operable to calculate a pressure difference between the single pressure measurement and the substantially constant pressure, the processing unit being further operable to calculate an expired volume based on a linear relationship between the expired volume and the pressure difference.

13. A method of determining a flow rate during respiration, comprising:
   allowing a fluid to flow through a duct, the duct including a restriction in the duct, the restriction being shaped symmetrically with respect to an axis perpendicular to a direction of flow such that, in operation, velocity of the fluid is substantially equal upstream and downstream of the restriction, and the duct with the restriction having a flow resistance;
   measuring a single pressure of the fluid proximate a patient end of the restriction;
   allowing the fluid to exit the duct through an outlet valve to a substantially constant pressure, the outlet valve having a flow resistance; and
   determining the flow rate based on the single pressure measurement relative to the substantially constant pressure and the respective flow resistances of the restriction and the outlet valve.

14. The method of claim 13, further comprising determining at least one of volume flow and mass flow of the fluid by integrating the measured flow rate over time.

15. The method of claim 13 wherein the substantially constant pressure is ambient pressure.

16. The method of claim 13 wherein determining the flow rate through the duct comprises determining a total resistance of the flow resistance through the restriction and the flow rate through the outlet valve in series to obtain total flow resistance, and determining a relative pressure difference between the measured pressure and the substantially constant pressure.

17. The method of claim 13 wherein determining the flow rate further comprises calculating a pressure difference between the single pressure measurement and the substantially constant pressure, and calculating an expired volume based on a linear relationship between the expired volume and the pressure difference.

* * * * *